US009931882B2

(12) United States Patent
Uyeno (10) Patent No.: US 9,931,882 B2
(45) Date of Patent: Apr. 3, 2018

(54) COUNTER COUNTERFEIT TECHNOLOGY (71) Applicant: Raytheon Company, Waltham, MA (US)

(72) Inventor: Gerald P. Uyeno, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 0 days.

(21) Appl. No.: 15/218,490

(22) Filed: Jul. 25, 2016

(65) Prior Publication Data
US 2018/0022144 A1 Jan. 25, 2018

(51) Int. Cl.
| | |
|---|---|
| *G06K 9/74* | (2006.01) |
| *B42D 25/328* | (2014.01) |
| *B42D 25/21* | (2014.01) |
| *B42D 25/382* | (2014.01) |
| *B42D 25/387* | (2014.01) |
| *B42D 25/445* | (2014.01) |
| *G01N 21/552* | (2014.01) |
| *G01N 21/65* | (2006.01) |
| *H01L 23/544* | (2006.01) |
| *G06K 7/10* | (2006.01) |
| *G06K 19/16* | (2006.01) |

(52) U.S. Cl.
CPC ........... *B42D 25/328* (2014.10); *B42D 25/21* (2014.10); *B42D 25/382* (2014.10); *B42D 25/387* (2014.10); *B42D 25/445* (2014.10); *G01N 21/553* (2013.01); *G01N 21/658* (2013.01); *G06K 7/10861* (2013.01); *G06K 19/16* (2013.01); *H01L 23/544* (2013.01); *H01L 2223/54433* (2013.01)

(58) Field of Classification Search
CPC ............ G06K 9/00046; G06K 9/00013; A61B 5/1172; G07D 7/12; G07D 7/122

USPC .......................................................... 356/71
See application file for complete search history.

(56) References Cited

U.S. PATENT DOCUMENTS

| | | | |
|---|---|---|---|
| 6,600,603 B1 | 7/2003 | Sambles | |
| 7,863,584 B2 | 1/2011 | Tardif et al. | |
| 9,179,542 B2 * | 11/2015 | Beck | ...................... G01N 21/65 |

(Continued)

FOREIGN PATENT DOCUMENTS

WO 9016043 A1 12/1990

OTHER PUBLICATIONS

Saman Jahani and Zubin Jacob, "All-dielectric metamaterials", nature nanotechnology, Focus Review Article, vol. 11, pp. 23-36, Jan. 2016.

*Primary Examiner* — Tarifur Chowdhury
*Assistant Examiner* — Md M Rahman
(74) *Attorney, Agent, or Firm* — Renner, Otto, Boisselle & Sklar, LLP (57) ABSTRACT An identification patch having a plasmonic resonance structure may be used to ensure that an article is counterfeit-proof. The identification patch may be formed by a printing process, such as roll-to-roll printing or nanoimprinting, to create a distinctive ordered pattern of resonance elements. When the plasmonic resonance structure is irradiated, the ordered pattern of resonance elements produces a unique spectral response that is associated only with the counterfeit-proof article. The counterfeit-proof article may be a metal component or an integrated circuit. The resonant absorption of the plasmonic resonance structure may be measured to verify the authenticity of the article before use of the article.

12 Claims, 4 Drawing Sheets (56) References Cited

U.S. PATENT DOCUMENTS

| | | |
|---|---|---|
| 2007/0165209 A1 | 7/2007 | Natan et al. |
| 2008/0282208 A1* | 11/2008 | Anderson ............... G06F 21/75 |
| | | 716/136 |
| 2009/0086291 A1* | 4/2009 | White ..................... B41M 5/00 |
| | | 358/502 |
| 2012/0217394 A1 | 8/2012 | Arruebo Gordo et al. |
| 2015/0221796 A1 | 8/2015 | Smith et al. |
| 2016/0231435 A1* | 8/2016 | Alvine .................. C23C 14/024 |
| 2016/0283834 A1* | 9/2016 | Bobbitt, III ............. B41M 3/14 |

* cited by examiner

COUNTER COUNTERFEIT TECHNOLOGY

FIELD OF THE INVENTION

The invention relates to a method and system for authenticating articles and for detecting counterfeit articles by way of a small piece of material attached to the article and a laser source and spectrometer.

DESCRIPTION OF THE RELATED ART

Various applications require verifying the authenticity of an article, such as a component or part, prior to use of the article. Particularly for safety and security purposes, authenticating the article ensures that the proper article is being provided for use in a particular application. For example, a computer processor is a component that may require authentication before use in a defense application. Using an improper or counterfeit article may result in failure of the article when used that can lead to degraded system performance or system failure.

Due to technology advances, the manufacturing of counterfeit articles has become easier and therefore more prevalent. Conventionally-used identifiers, such as silk-screen serial numbers and barcodes, may be easy to copy or replicate.

SUMMARY OF THE INVENTION

An identification patch of material having distinctive optical properties may be used to ensure that an article is counterfeit-proof. The identification patch has a nanometer scale structure with a well-defined pattern of elements of conducting material formed by way of a roll-to-roll printing process. When subject to light of the appropriate wavelength, the patch has distinctive optical response associated with the plasmonic resonance, such as a specific absorption spectrum. When the identification patch is formed, desired optical properties, such as the specific absorption spectrum, are measured and specific data pertaining to the properties is stored in a database. The identification patch is then attached to the article and the article is transported or stored for later use. The article may be a metal component or an integrated circuit or use in a particular application. Before use of the article, the patch is irradiated with light of the appropriate wavelength and the desired optical properties, such as the specific absorption spectrum, are measured. The data stored in the database is accessed to verify that the measured data matches the stored data and that the article is authentic.

Using the distinctive pattern of resonance elements as a counterfeit technology is advantageous in that the identification patch has a unique optical signature that may be difficult to replicate. The identification patch may also be formed to have a particular optical signature within a specific portion of the electromagnetic spectrum, such as the ultraviolet, visible, or infrared light region. Another advantage is that the identification patch may be cost-effectively manufactured, based on the varying materials that may be used. Using the roll-to-roll printing process is also cost-effective in that the process enables the forming of a meter scale sheet of material with nanoscale features in several minutes. The patches can be as small as a few millimeters on a side, so the meter scale sheet of material will yield 1000s of patches. In addition to cost-effectiveness, another advantage of using the roll-to-roll printing process is that even the slightest variations in rollers or materials may create distinctive patterns in each of the patches. If the spectrometer has sufficient resolution, variations of each patch due to local variations in the manufacturing process along with distinctive patterns due to the variations will enable each of these patches to have unique optical properties. Still another advantage of using the plasmonic resonance structure is that the identification patch may also be used in conjunction with conventionally-used identifiers, such as barcodes, to provide a further verification step to authenticate the component. Another advantage is that multiple patches, with different wavelengths may be combined to provide a further verification. Using the plasmonic resonance structure for additional verification may be particularly advantageous for components used in defense and medical applications.

According to an aspect of the invention, a counterfeit-proof article includes an exterior surface and at least one identification patch of material attached to the exterior surface. The identification patch of material has an ordered pattern of plasmonic resonance elements that produce a distinctive optical response in an electromagnetic spectrum. The ordered pattern of plasmonic resonance elements produces a measurable Raman shift.

According to an aspect of the invention, the plasmonic resonance elements may be equidistantly spaced and have a rectangular, cubic, hemi-spherical or disc shape.

According to an aspect of the invention, the plasmonic resonance elements may be shaped as pyramidal shaped ridges, pyramidal teeth, circular or rectangular pillars, or circular or rectangular posts.

According to an aspect of the invention, the at least identification patch of material may have a length between 1 and 5 millimeters and a width between 1 and 5 millimeters.

According to an aspect of the invention, the counterfeit-proof article may include a plurality of identification patches of material attached to the exterior surface, each of the plurality of identification patches of material having a distinctive ordered pattern of plasmonic resonance elements.

According to an aspect of the invention, the counterfeit-proof article may include a serial number, barcode, or hologram attached to the exterior surface in addition to the at least one identification patch of material.

According to an aspect of the invention, the counterfeit-proof article may be an integrated circuit.

According to an aspect of the invention, a method for producing a counterfeit-proof article includes using a printing process using a printing process to form an ordered pattern of plasmonic resonance elements on a sheet of material, cutting the sheet to form at least one patch containing a portion of the ordered pattern, and attaching the at least one patch to a surface of the article, where the ordered pattern of plasmonic resonance elements produces a distinctive optical response in an electromagnetic spectrum.

According to an aspect of the invention, the method may include roll-printing a sintered ceramic material and coating the ceramic material with an electrically conductive material.

According to an aspect of the invention, the method may include forming the ordered pattern of doped ceramic resonance elements on the sheet formed of polymeric material.

According to an aspect of the invention, the method may include roll-printing a conductive liquid polymeric material and curing the conductive liquid polymeric material with an ultraviolet light.

According to an aspect of the invention, using a printing process may include using a nanoimprinting process to form the ordered pattern of resonance elements.

According to an aspect of the invention, an article has an identification patch disposed on a surface of the article and the identification patch is formed of a printed plasmonic resonance structure. A method of authenticating the article includes irradiating the identification patch using a light source having at least one specific wavelength, measuring an absorption spectrum of the printed plasmonic resonance structure at the at least one specific wavelength, detecting a measured data point on the absorption spectrum, comparing the measured data point to a reference data point corresponding to the absorption spectrum of the printed plasmonic resonance structure, and verifying the measured data point with the reference data point to authenticate the article.

According to an aspect of the invention, the method of authenticating the article may include detecting a peak portion of the absorption spectrum to identify the specific wavelength that is preferentially absorbed by the printed plasmonic resonance structure.

According to an aspect of the invention, the method of authenticating the article may include comparing the specific wavelength to a reference specific wavelength corresponding to the printed plasmonic resonance structure.

According to an aspect of the invention, detecting the peak portion of the absorption spectrum may include detecting a narrowest point of an absorption band to identify the specific wavelength.

According to an aspect of the invention, measuring the absorption spectrum may include using a measured Raman shift.

According to an aspect of the invention, the method of authenticating the article may include measuring the absorption spectrum of each of a plurality of identification patches disposed on the article to authenticate the article, where each of the plurality of identification patches has a different printed plasmonic resonance structure.

According to an aspect of the invention, the method of authenticating the article may include locating a second identifier disposed on the article, comparing the second identifier to a reference second identifier corresponding to the article, and verifying the second identifier with the reference second identifier to further authenticate the article before or after authenticating the article using the printed plasmonic resonance structure.

According to an aspect of the invention, the method of authenticating the article may include using a barcode or a hologram as the second identifier.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

The annexed drawings, which are not necessarily to scale, show various aspects of the invention.

DETAILED DESCRIPTION

The principles described herein have application for authenticating any suitable article in various applications. Examples of suitable articles include manufactured parts or components and paper documents. Examples of paper documents include contracts, checks, passports, birth certificates, driver's licenses, medical forms, paper currency, and any type of legal document or personal identification document. Other suitable articles may include commercial products. In defense applications, various parts or components may require authentication prior to use. Producing a counterfeit-proof article may include manufacturing a roll-to-roll printed patch of material with a plasmonic resonance structure and attaching the patch of material to the article. The plasmonic resonance structure has an ordered pattern of resonance elements that produces a distinctive and measurable optical properties to enable verification of the authenticity of the article.

Figure 1:
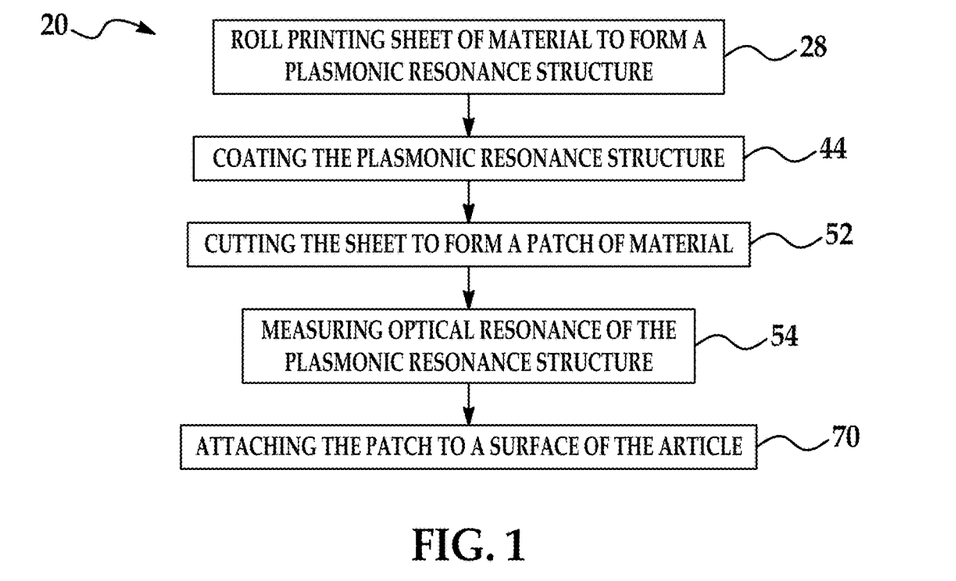
FIG. 1 is a flow chart illustrating a method of producing a counterfeit-proof article.
Figure 2:
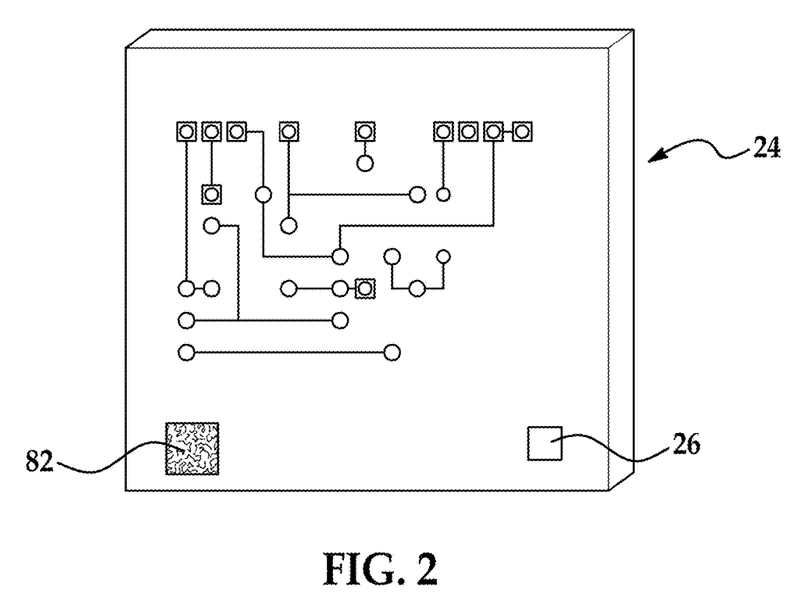
FIG. 2 is a schematic drawing showing an oblique view of an exemplary counterfeit-proof article.
Figure 3A:
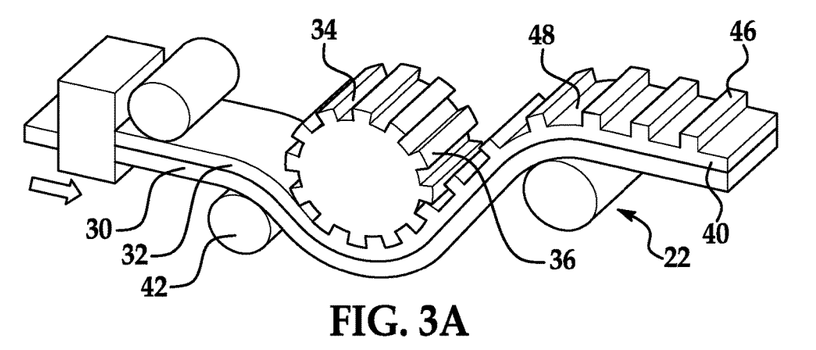
FIG. 3A is a schematic drawing showing an oblique view of a system for producing the counterfeit-proof article.
Figure 3B:
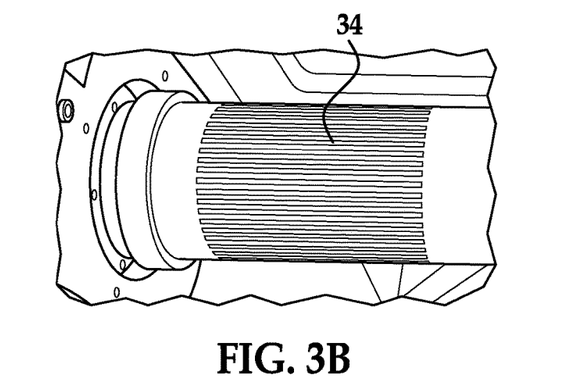
FIG. 3B is a schematic drawing showing an oblique view of a detailed portion of the system of FIG. 3A.

Referring now to FIGS. 1-4, a method 20 and a system 22 for producing the counterfeit-proof article 24 are schematically illustrated. FIG. 1 is a flow chart illustrating the method 20 for producing the counterfeit-proof article 24 and FIG. 2 is a schematic drawing of the counterfeit-proof article 24 with an identification patch 26 of material. The exemplary counterfeit-proof article 24 is schematically shown as an integrated circuit, but the counterfeit-proof article 24 may be any component, part, module, or suitable article. The counterfeit-proof article 24 may be a metal component. In addition to the identification patch 26, the counterfeit-proof article 24 may also include a second identifier 28, such as a conventionally-used barcode. FIG. 3 is a schematic drawing of the exemplary system 22 used to produce the identification patch 26 having a plasmonic resonance structure. The system 22 may include using a roll-to-roll printing machine and process. The roll-to-roll printing process is an exemplary process for producing the identification patch 26 and any suitable printing method or process may be used to produce a patch of material having a plasmonic resonance structure.

The method 20 is an exemplary method for producing the counterfeit-proof article 24. The method 20 includes roll printing a sheet of material, but any suitable printing method or process may be used. As best shown in FIG. 3, step 30 of the method 20 includes roll printing a sheet of material 32 to form a mold, or the identification patch 26. The sheet of material 32 may be formed of any suitable material. For example, the sheet of material 32 may be in the form of a thin film of polymeric or ceramic material. FIG. 3 shows an exemplary sheet of material 32 formed of a flexible polymeric material. Other examples of suitable materials used to form the identification patch 26 may include a wafer configuration formed of silicon, germanium, cadmium telluride, cadmium zinc telluride, or gallium arsenide.

Figure 4:
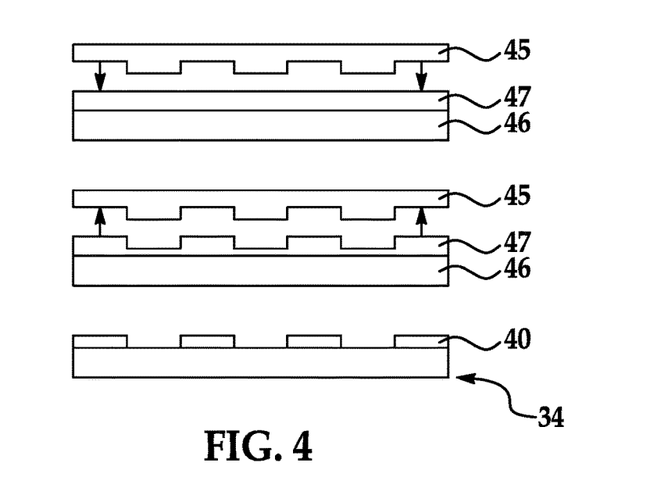
FIG. 4 is a schematic drawing showing an oblique view of an exemplary process for producing the counterfeit-proof article.

The sheet of material 32 may have any suitable dimensions. An example of suitable dimensions for the sheet of material 32 are a width of around 20 centimeters and a length of around 91 centimeters. The thickness of the sheet of material 32 may be less than 1 millimeter. Step 30 may include using roll-to-roll production tools for direct printing of the plasmonic resonance structure 34 on the sheet of material 32, as schematically shown in the system 22 of FIG. 3. The system 22 may include at least one rotatable roller 36. As best shown in FIGS. 3 and 4, the roller 36 may be cylindrical in shape and have a plurality of protrusions 38 for forming a plurality of resonance elements 40 on the plasmonic resonance structure 34. During rotation of the roller 36, the sheet of material 32 may be threaded through a plurality of secondary rollers 42 to maintain tension in the sheet of material 32, particularly if the sheet of material 32 is formed of a plastic material. The rollers 42 may be located above and/or below the sheet of material 32. The rollers 26, 42 may be nano-scale sized rollers.

Using the roll-to-roll process for printing the nanoscale material to the sheet of material 32 is advantageous in that roll-to-roll printing is cost-effective. For example, the sheet of material 32 having a width of around 20 centimeters and a length of around 91 centimeters may be produced in several minutes. The sheet of material 32 may be cut to form 1000s of patches having widths and lengths between 1 and 5 millimeters. Using roll-to-roll printing is also advantageous in that the process enables many distinctive patterns of the resonance elements 40, such that a particular pattern may be selected to produce a distinctive optical response in a desired portion of the electromagnetic spectrum. The materials and ordered pattern of the resonance elements 40 may be selected to produce an optical response in an ultraviolet, infrared, or visible light region of the electromagnetic spectrum. The slightest variations in roller dimensions or properties of the materials may create distinctive patterns. Roll-to-roll-printing is an exemplary manufacturing process and any suitable manufacturing process may be used to print the plasmonic resonance structure 34 to the sheet of material 32. Examples of other suitable manufacturing methods include subtractive processing using silicon wafer-based platforms and pulse flash lamp cure technology.

The plasmonic resonance structure 34 may be formed of any suitable material, such as a ceramic material. The ceramic material may be sintered. The ceramic material may be a metal oxide, such as titanium dioxide and indium tin oxide. The ceramic material may be doped with rare earth materials. A plasmonic resonance structure that is formed of a doped metal oxide may not have a coating of additional electrically conductive material, but an optional step 44 of the method 20 may include coating a top surface of a sintered ceramic material with any suitable electrically conductive material. An example of a suitable coating material may be silver and the coating may have a thickness of less than 1 micron. In another configuration of materials, the plasmonic resonance structure 34 may be formed of a liquid conductive polymeric material that is roll-printed to a sheet of polymeric material. The liquid may be cured after printing. In still another configuration of materials, two block copolymers may be used for roll-printing. The blocks of copolymers may self-assemble into ridges and polka dot shaped resonance structures. The material used to form the plasmonic resonance structure 34 during the roll-to-roll printing process may be selected to produce an optical response in a particular portion of the electromagnetic spectrum. For example, using indium tin oxide with dopants may produce a distinctive optical response in a mid-infrared light region of the electromagnetic spectrum.

Referring now to FIG. 4, an exemplary process for forming the plasmonic resonance structure 34 is schematically shown. The plasmonic resonance structure 34 may be formed by a nanoimprinting process. Nanoimprinting may be advantageous in that it is a cost-effective process that may produce nanostructures having a high resolution. The nanoimprinting process may be performed by a suitable machine or tools. The process may be used to produce discs used in forming the identification patch 26. The discs may have a diameter that is between 20 and 22 centimeters. As shown in FIG. 4, the process includes using a 20 to 22 centimeter diameter positive master disc, or mold 45 having a desired pattern for forming the resonance elements 40. Another 20 to 22 centimeter plate 46 of substrate material is then covered with a uniform layer of photoresist 47, a light-sensitive material. The positive master disc 45 may be pressed into the plate 46 of substrate material, and then removed such that a pattern is formed in the photoresist 47. The photoresist 47 may be thinner in particular regions where a complementary portion of the master disc 45 is thicker. The formed plate covered with the patterned photoresist 47 may then be cured by exposure to ultraviolet light. The formed plate may be exposed for a time that is long enough such that in regions where the photoresist is thinner, all of the photoresist material and some of the substrate is exposed, and short enough such that the substrate is not exposed in regions where the photoresist is thicker. After curing, the substrate 46 may be etched using anistoropic etching to remove portions of the substrate that were exposed and generate the desired plasmonic resonance structure 34 having resonance elements 40.

Figure 5:
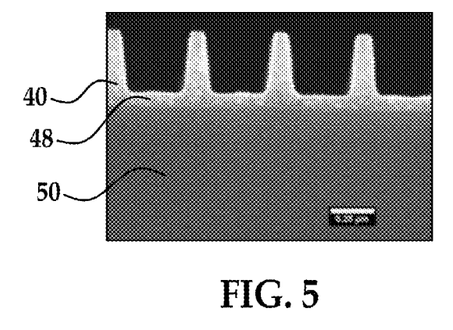
FIG. 5 is a drawing showing a detailed view of a plasmonic resonance structure formed by the method of FIG. 1.

Referring in addition to FIG. 5, the plasmonic resonance structure 34 is formed to have an ordered pattern of the resonance elements 40. Each resonance element 40 may include a top surface for absorbing photons when the plasmonic resonance structure 34 is irradiated by a light source. As best shown in FIG. 5, the plasmonic resonance structure 34 may include a semiconductor photon absorber layer 48 that has an energy bandgap responsive to radiation in a spectral region of interest. The plasmonic resonance structure 34 may also include a semiconductor collector layer 50 that is coupled to the absorber layer 48. When the plasmonic resonance structure 34 is irradiated, the plasmonic resonance structure 34 operates by resonating incident flux, causing a field to be built up in the absorber layer 48. The interaction between electromagnetic waves and surface charges of the resonance elements 40 increases momentum of the surface plasmon polariton, deviating from the momentum of incident light through air. When the moment of incident light from the light source and the surface plasmon matches, resonance will occur in the resonance elements 40.

Figure 6:
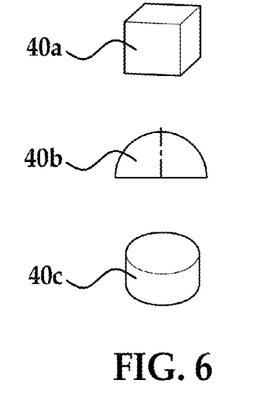
FIG. 6 is a schematic drawing showing an oblique view of exemplary resonance structures that may be formed by the method of FIG. 1.

Referring in addition to FIG. 6, forming the pattern of the resonance elements 40 may include equidistantly spacing the resonance elements 40. The resonance elements 40 may be periodically spaced and shaped to form a pattern that focuses plasma waves into the absorber layer 48. The pattern of the plasmonic resonance structure 34 may be varied on a per pixel basis, to provide individualized spectral and/or polarization responses for the pixels of a particular detector array used to measure the optical properties of the resonance elements 40. The resonance elements 40 may be arranged to achieve a desired wavelength selectivity or polarization selectivity. The resonance elements 40 may have any suitable shape and dimensions and may be configured to produce a distinctive optical response in a particular portion of the electromagnetic spectrum. Examples of suitable shapes are protrusions such as pyramidal shaped ridges, pyramidal teeth, circular or rectangular pillars, or circular or rectangular posts.

The resonance elements 40 may include additional features located on a top portion of each pillar or post. As shown in FIG. 6, the resonance elements 40 may have a cubic shape 40a, hem i-spherical shape 40b, or a cylindrical shape 40c. Hem i-spherical shapes may be advantageous in that the shape enables the structure to easily be released from a mold. Many other suitable shapes may be formed and the shape may be dependent on the material used. A sintered powder material may be used. For example, a roll-printed sintered ceramic material that is coated with conductive material may be formed in the shape of ridges. A roll-printed doped ceramic material or a roll-printed conductive liquid polymer may also be in the shape of ridges. The resonance elements 40 may have a height of around 1 micron and a width of around 0.10 microns, although these dimensions are only examples, and may other heights and/or widths are possible. The resonance elements 40 may extend perpendicularly to the absorber layer 48 of the resonance structure 32 and may be arranged in any suitable ordered configuration. Examples of suitable configurations are arrays and gratings.

After the plasmonic resonance structure 34 having the pattern of resonance elements 40 is formed on the sheet of material 32, step 52 of the method 20 for producing the counterfeit-proof article includes cutting the sheet of material 32 to form at least one identification patch 26 to be attached to the article 24. The identification patch 26 includes a portion of the pattern of the resonance elements 40 formed on the sheet of material 32. The identification patch 26 may have any suitable size and the size of the patch 26 may be dependent on the article to which the identification patch 26 is to be attached. The identification patch 26 may have any suitable shape. Examples of suitable shapes include rectangular and circular or disc-shaped. Cutting the sheet of material 32 may include forming the identification patch to have a length between 1 and 5 millimeters and a width between 1 and 5 millimeters. Step 52 may also include cutting the sheet of material 32 to form a plurality of identification patches that each have a distinctive ordered pattern of resonance elements 40.

Step 54 of the method 20 includes measuring optical properties of the plasmonic resonance structure 34 and storing the measured data. Measuring the optical properties may include measuring a response of the plasmonic resonance structure 34 to light, such as measuring the resonant absorption of the plasmonic structure 34. The optical properties of the plasmonic resonance structure 34 may be measured before or after the sheet of material 32 is cut to form the at least one identification patch 26. Each sheet of material 32 may have a plasmonic resonance structure 34 with a different ordered pattern of resonance elements 40, creating a unique optical resonance for each sheet of material 32. As previously described, roll-to-roll printing enables each sheet of material 32 to have a distinctive pattern of resonance elements 40. For example, a material having a first particle size may result in a first resonance structure that has a first pattern of resonance elements. A second resonance structure may be formed from the same material, but the material may have different particle sizes than the first particles size. The resonance structures may be printed by the same roller, but even a slight difference in the material properties, such as particle size, may result in a distinctively patterned resonance structure.

Figure 7:
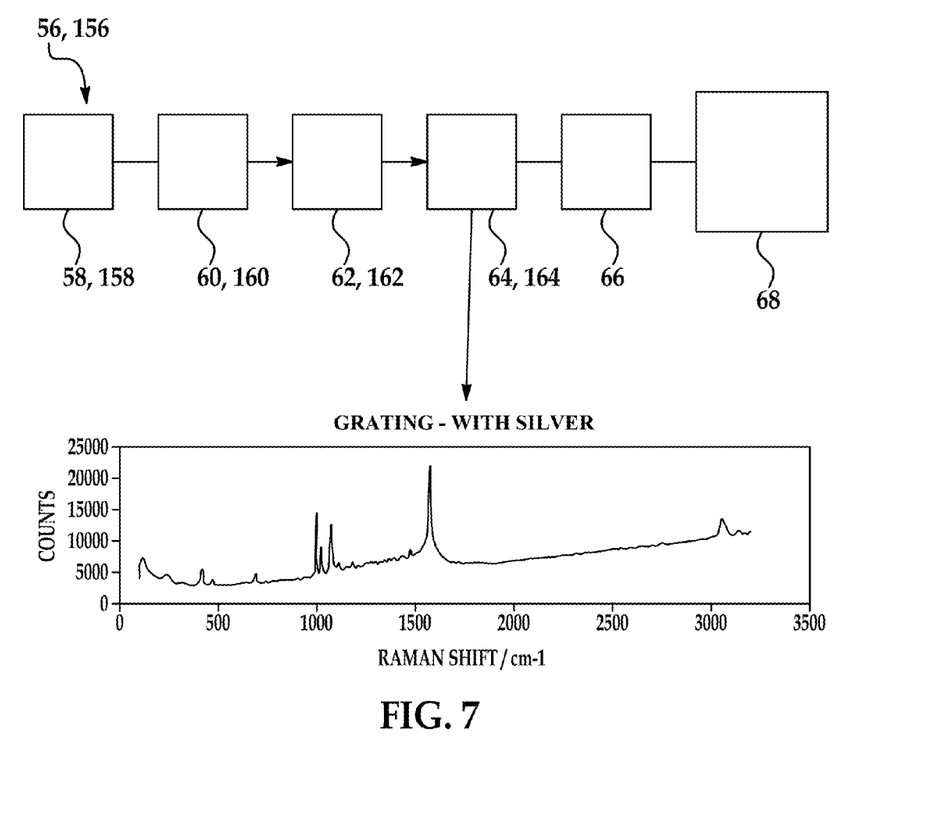
FIG. 7 is a schematic drawing showing a system for measuring optical properties of the plasmonic resonance structure formed by the method of FIG. 1.

Any suitable system may be used for measuring the optical properties of the plasmonic resonance structure 34. Components of the system may be dependent on the optical property being measured. An exemplary system 56 is schematically shown in FIG. 7. The system 56 may include a light source 58 for irradiating the identification patch 26. The light source 58 may be any suitable light source for shining light on the identification patch 26 and the form of the light source 58 may be dependent on the materials of the identification patch 26. The light source may be dependent on the optical response produced by the identification patch 26. For example the type of light source may be dependent on whether the plasmonic resonance structure 34 produces an optical response in an ultraviolet, visible, or infrared light region of the electromagnetic spectrum. An example of a suitable light source for irradiating the identification patch 26 formed by the roll-to-roll process is an infrared laser, but many other types of light sources may be used. The light source may be operable at a wattage of less than 1. For an identification patch that is formed of a cured polymeric material, the light source 58 may be an ultraviolet light, such that the polymeric material reacts to the ultraviolet light to provide a measurable response. The light source 58 may be operable at various wavelengths. As best shown in FIGS. 5 and 6, in response to incident radiation in a z-direction, which is generally normal to the top surface of the resonance elements 40, the plasmonic resonance structure 34 causes a resonance in the x-y plane, allowing the absorber layer 48 to collect substantially all photons and maintain a high quantum efficiency.

The system 56 may include a spectrometer 60 for measuring the optical properties of the plasmonic resonance structure 34. The spectrometer 60 may be configured to measure any suitable optical spectrum, such as the spectrum pertaining to the absorption of the light from the light source 58 by the plasmonic resonance structure 34. The ordered pattern of the plasmonic resonance structure 34 may have a distinctive optical response in an ultraviolet, visible, or infrared light region of the electromagnetic spectrum. The ordered pattern and materials of the plasmonic resonance structure 34 may be selected to produce a distinctive optical response in a desired region of the electromagnetic spectrum.

When the patch 26 is irradiated, the plasmonic resonance structure 34 may absorb light at predetermined wavelengths of the light source 58. Light that is not transmitted is absorbed by the plasmonic resonance structure 34. As graphically illustrated in FIG. 7, the plasmonic resonance structure 34 is formed to have a specific absorption spectrum 59 such that the spectrometer 60 may detect a peak portion 59a of the absorption spectrum 59 to identify a specific wavelength of the absorption spectrum 59 that is preferentially absorbed by the plasmonic resonance structure 34. The specific wavelength may be used as a reference data point associated with the plasmonic resonance structure 34 since the specific wavelength is unique to the absorption spectrum 59 associated with the plasmonic resonance structure 34. Detecting the peak portion 59a of the absorption spectrum 59 may include detecting a narrowest point of an absorption band 59b to identify the specific wavelength.

After the spectrometer 60 has measured the desired optical spectrum, the system 56 includes a detector 62 that may be part of the spectrometer 60 for converting the measured spectrum into an electrical signal that may be viewed and analyzed using a processor 64. The detector 62 may be configured to receive an analog output from the spectrometer 60 regarding the absorbance spectrum 59 of the plasmonic resonance structure 34. As shown in FIG. 7, the processor 64 may be configured to produce an output of data points 59c of the absorbance at different wavelengths of the light source 58. The specific data points of the absorption spectrum 59 may be calculated using any suitable algorithm, such as equation (1). Equation (1) is an example of an equation that may be used by the processor 64 to calculate the specific data points of the absorption spectrum 59.

$$A(\lambda) = \in(\lambda) * l * c \quad (1)$$

With regards to equation (1), the value $A(\lambda)$ is the absorption of the plasmonic resonance structure 34 calculated as a function of wavelength. The value $\in(\lambda)$ (L/mol*cm) is the molar absorptivity or extinction coefficient of the absorbing molecule as a function of wavelength. The proportion of the light absorbed may depend on how many molecules interact with the light such that value c (mol/L) is the concentration of the molecules in the irradiated plasmonic resonance structure 34. The value l (cm) is the path length traveled by light through the irradiated surface. Equation (2) is another example of an algorithm that may be used by the processor 64 to calculate specific data points of the absorption spectrum 59.

$$A = \log_{10}(P_0/P) \quad (2)$$

With regards to equation (2), the value $P_0$ is the amount of radiant power from a beam of light directed at a surface of the plasmonic resonance structure 34 and P is the radiant power of the beam of radiation leaving the surface.

The spectrometer 60, the detector 62, and the processor 64 may be configured to measure any suitable spectral data associated with the plasmonic resonance structure 34 and output at least one specific data point associated with the optical resonance of the resonance structure 32. As shown in FIG. 7, measuring the absorption of the light may include using Raman spectral data of the plasmonic resonance structure 34. The spectrometer 60 may be configured to measure Raman scattering, or the inelastic scattering of the photons that strike the molecules of the surface of the plasmonic resonance structure 34. When a molecule takes up energy from or gives up energy to the photons, the photons are scattered with diminished or increased energy, and lower or higher frequency. The frequency shifts are measures of amounts of energy involved in the transition between initial and final states of the scattering molecule. The detector 62 and the processor 64 may be configured to calculate Raman shifts using equation (3) and output the calculated data points, as shown in FIG. 7.

$$\Delta w = (1/\lambda_0 - 1/\lambda_1) \quad (3)$$

With regards to equation (3), the value $\Delta w$ is the Raman shift in wavenumber, $\lambda_0$ is the excitation wavelength and Ai is the Raman spectrum wavelength. The Raman spectral data shown in FIG. 7 is associated with an exemplary plasmonic resonance structure having silver coated resonance elements, but the Raman spectral data for any plasmonic resonance structure may be measured.

After the optical properties of the plasmonic resonance structure 34 have been measured by the spectrometer 60 and the detector 62, the processor 64 is also configured to associate a specific data point corresponding to the measured optical properties, such as the absorption spectrum 59, with the article 24. For example, the specific data point may be a wavelength of the light source 58 on the absorption spectrum 59 where light is not absorbed by the plasmonic resonance structure 34. The entire absorption spectrum 59 may also be used as the specific data point, where the absorption spectrum 59 acts as a "fingerprint" or a unique optical signature for the plasmonic resonance structure 34.

The specific data point may be any suitable information that is associated with the particular pattern of the resonance elements 40 of the plasmonic resonance structure 34. The range of wavelengths where the data is measured may be dependent on the size, shape, and material of the resonance elements 40 and the resonance elements 40 may be patterned to obtain particular optical properties. For example, a 3D array of spherical shaped dielectric resonance elements 40 having a radius of 0.5 centimeters may have measurable spectral data between wavelengths of 0.4 and 0.7 microns. In another example, a 2D array of cubic tellurium resonators having a length of 1.45 microns may have measurable spectra data between wavelengths of 6 and 11 microns. In still another example, silicon disc shaped resonators may have measurable spectral data between wavelengths of 0.9 and 1.6 microns. In still another example, a plasmonic resonance structure 34 may be formed of pillars having hemi-spherical portions on top of the pillars. The hemi-spherical portions may be coated with silver for measurable spectral data in a short wave infrared region.

When the specific data point is calculated and determined by the processor 64, the processor 64 may include a database 66 for storing the specific data point and/or the entire measured optical spectrum associated with the identification patch 26 and the article 24. The specific data point and/or the entire measured optical spectrum serve as identifying information, or a reference data point, for the article 24. The database 66 may be in communication with a network 68 of processors and systems that are configured to measure optical properties of the identification patch 26. The database 66 may be accessed at a later point in time when the authenticity of the article 24 is to be verified.

After the optical data corresponding to the article 24 has been stored in the database 66, step 70 of the method 20 for producing the counterfeit-proof article includes attaching the identification patch 26 to the article 24. The patch 26 may be attached using any suitable adhesive or fastening mechanism. A surface of the identification patch 26 that is opposite the plasmonic resonance structure 34 may be configured as the attachment surface. The attachment mechanism may be dependent on the interface between the article 24 and the attachment surface. The attachment surface of the patch 26 may be formed of the material of the sheet of material 30, such that the attachment surface may be formed of a polymeric or ceramic material. For adhering a polymeric or ceramic material to a metal article, an example of a suitable adhesive may be an epoxy adhesive. Examples of suitable fastening mechanisms may include threaded fasteners, clamps, and pins.

The method 20 may be repeated to form a plurality of identification patches 26 and attach the plurality of identification patches 26 to the article 24. Each of the plurality of identification patches 26 may have a different wavelength. After at least one identification patch 26 is attached to the article 24, the counterfeit-proof article 24 may be stored for later use or transported from the location where it is produced to another location where it is intended to be used. For example, the counterfeit-proof article 24 may be a part that is produced at a production facility and transferred to another manufacturing facility. When the part is received at the manufacturing facility, the part may be authenticated before being used or implemented in another application. The part may also be stored for a period of time, such that authentication of the part may be desirable before use.

Figure 8:
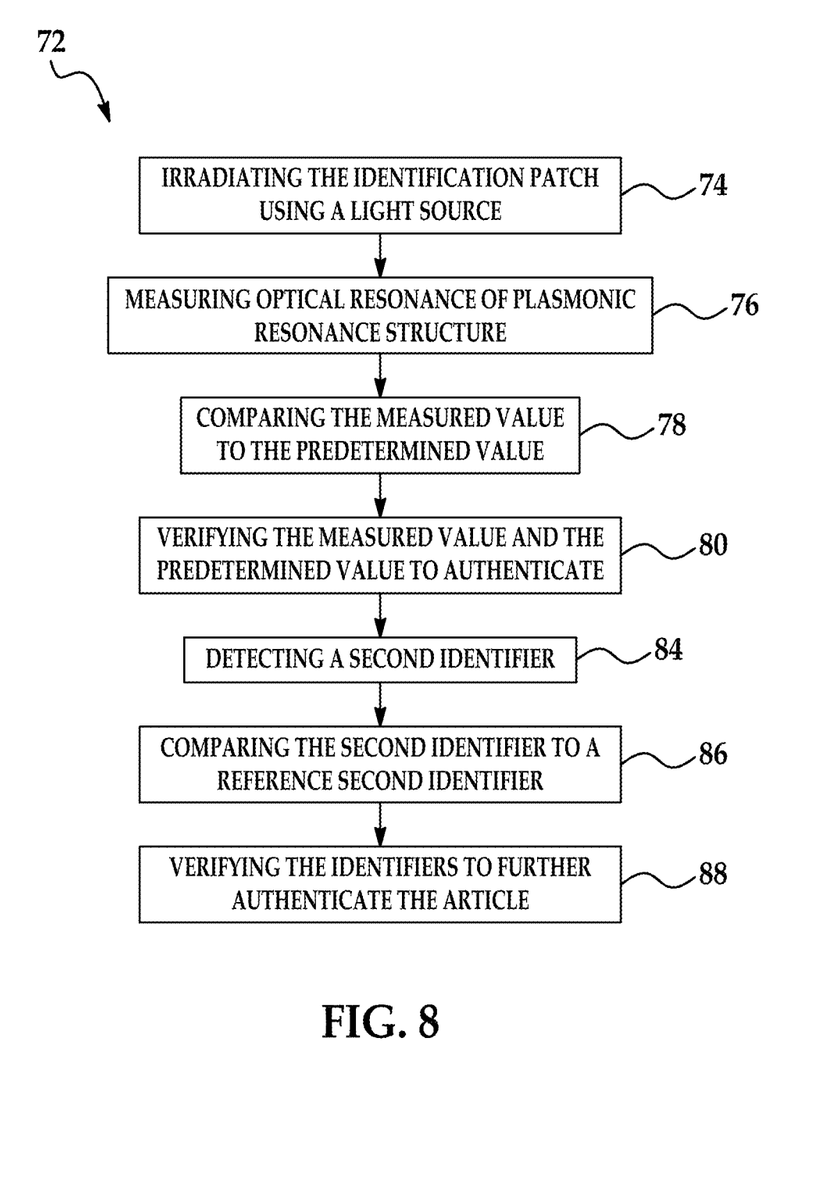
FIG. 8 is a flow chart illustrating a method of authenticating the counterfeit-proof article formed by the method of FIG. 1.

Referring now to FIG. 8, a method 72 of authenticating the counterfeit-proof article 24 is schematically shown in a flowchart. As shown in FIG. 7, the method 72 may include using a counterfeit detecting system 156 for detecting the authenticity of the article. The counterfeit detecting system 156 may be similar to the system 56 used for measuring the optical properties of the plasmonic resonance structure 34. Step 74 of the authentication method 72 includes irradiating the identification patch using a light source 158, as previously described. Step 76 includes measuring optical properties of the plasmonic resonance structure 34 on the identification patch 26. The counterfeit detecting system 156 may include a spectrometer 160, a detector 162, and a processor 164 for measuring the desired optical properties of the plasmonic resonance structure 34 and determining at least one specific data point associated with the optical properties. As previously described, the specific data point may be a wavelength on the absorption spectrum where light is preferentially absorbed by the plasmonic resonance structure 34, or the absorption spectrum itself.

The spectrometer 160, the detector 162, and the processor 164 may be similar to those previously described in the system 56. After the specific data point is measured and determined, step 78 of the method 72 includes comparing the measured data point to the reference data point that was obtained by the system 56. The processor 164 of the counterfeit detecting system 156 may be configured to compare the data points. More than one data point may be used. For example the processor 164 may be configured to compare the measured absorption spectrum with the reference absorption spectrum. The processor 164 may be in communication with the database 66, as part of the network 68 of processors that are in communication with the database 66. After comparing the values, step 80 of the method 72 may include verifying the measured data point with the reference data point to authenticate the article 24. The processor 164 may be configured to produce an output indicating whether the article 24 is a counterfeit article. If the article 24 has a plurality of identification patches 26, the method 72 may be repeated for each identification patch 26.

The method 72 and system 156 may further be configured to detect or read the second identifier 28 on the article 24, as shown in FIG. 2. Step 84 of the method 72 may include detecting the second identifier 28 disposed on the article 24. For example, the second identifier 28 may be in the form of a serial number, 1D barcode, 2D barcode, hologram, silk-screened serial numbers, or any suitable identifier. The second identifier 28 may be disposed on a surface of the article 24 and data corresponding to the second identifier 28 and the article 24 may be stored in the database 66 such that the second identifier 28 may be verified with the stored data. After detecting the second identifier 28, step 86 may include comparing the second identifier 28 to a reference second identifier corresponding to the article 24 that is stored in the database 66. The processor 164 may be configured to compare the identifiers. After comparing the identifiers, step 88 may include verifying the second identifier 28 with the reference second identifier 28 to further authenticate the article 24, before or after authenticating the article 24 using the identification patch 26. Using the second identifier 28 in conjunction with the identification patch 26 enables additional authentication of the article 24 prior to use.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A counterfeit-proof article comprising:
   an exterior surface; and
   at least one identification patch of material attached to the exterior surface, the identification patch of material having a plasmonic resonance structure, the plasmonic resonance structure having an absorber layer and an ordered pattern of plasmonic resonance elements that protrude from the absorber layer and that produce a distinctive optical response in an electromagnetic spectrum,
   wherein the ordered pattern of plasmonic resonance elements produces a measurable Raman shift,
   wherein the plasmonic resonance structures is formed of a metal oxide that is doped with a rare earth metal,
   wherein the plasmonic resonance elements are equidistantly spaced, and
   wherein each of the plasmonic resonance elements have a height of around 1 micron and a width of around 0.10 microns.

2. The counterfeit-proof article of claim 1, wherein the plasmonic resonance elements have a rectangular, cubic, hemi-spherical or disc shape.

3. The counterfeit-proof article of claim 1, wherein the plasmonic resonance elements are shaped as pyramidal shaped ridges, pyramidal teeth, circular or rectangular pillars, or circular or rectangular posts.

4. The counterfeit-proof article of claim 1, wherein the at least one identification patch of material has a length between 1 and 5 millimeters and a width between 1 and 5 millimeters.

5. The counterfeit-proof article of claim 1, wherein the counterfeit-proof article includes a serial number, barcode, or hologram attached to the exterior surface in addition to the at least one identification patch of material.

6. The counterfeit-proof article of claim 1, wherein the counterfeit-proof article is an integrated circuit.

7. The counterfeit-proof article of claim 1, wherein the plasmonic resonance elements are periodically spaced to focus plasma waves into the absorber layer.

8. The counterfeit-proof article of claim 1, wherein the plasmonic resonance elements extend perpendicularly to the absorber layer.

9. The counterfeit-proof article of claim 1, wherein the identification patch has a shape that is rectangular or circular or disc-shaped.

10. A counterfeit-proof article comprising:
    an exterior surface; and at least one identification patch of material attached to the exterior surface, the identification patch of material having a plasmonic resonance structure, the plasmonic resonance structure having an absorber layer and an ordered pattern of plasmonic resonance elements that protrude from the absorber layer and that produce a distinctive optical response in an electromagnetic spectrum, wherein the ordered pattern of plasmonic resonance elements produces a measurable Raman shift, wherein the at least one identification patch of material has a length between 1 and 5 millimeters and a width between 1 and 5 millimeters, wherein the counterfeit-proof article includes a plurality of identification patches of material attached to the exterior surface, each of the plurality of identification patches of material having a distinctive ordered pattern of plasmonic resonance elements, and wherein the counterfeit-proof article includes a serial number, barcode, or hologram attached to the exterior surface in addition to the at least one identification patch of material.

11. A counterfeit-proof article comprising:
an exterior surface; and
at least one identification patch of material attached to the exterior surface, the identification patch of material having a plasmonic resonance structure, the plasmonic resonance structure having an absorber layer and an ordered pattern of plasmonic resonance elements that protrude from the absorber layer and that produce a distinctive optical response in an electromagnetic spectrum, wherein the ordered pattern of plasmonic resonance elements produces a measurable Raman shift, wherein the at least one identification patch of material has a length between 1 and 5 millimeters and a width between 1 and 5 millimeters, wherein the plasmonic resonance structure is formed of a ceramic material and has a top surface that is coated with an electrically conductive material, and wherein the plasmonic resonance elements each have a height of around 1 micron and a width of around 0.10 microns.

12. The counterfeit-proof article of claim 11, wherein the identification patch includes a polymeric sheet of material, and the ordered pattern of plasmonic resonance elements are formed on the polymeric sheet of material.

* * * * *